(12) United States Patent  
Stetter et al.

(10) Patent No.: US 8,795,484 B2
(45) Date of Patent: Aug. 5, 2014

(54) PRINTED GAS SENSOR

(71) Applicant: KWJ Engineering, Inc., Newark, CA (US)

(72) Inventors: Joseph R. Stetter, Hayward, CA (US); Edward F. Stetter, North Aurora, IL (US); Daniel D. Ebeling, Wauwatosa, WI (US); Melvin Findlay, Fremont, CA (US); Vinay Patel, Fremont, CA (US)

(73) Assignee: KWJ Engineering, Inc., Newark, CA (US)

( * ) Notice: Subject to any disclaimer, the term of this patent is extended or adjusted under 35 U.S.C. 154(b) by 0 days.

(21) Appl. No.: 13/740,327

(22) Filed: Jan. 14, 2013

(65) Prior Publication Data

US 2013/0126069 A1    May 23, 2013

Related U.S. Application Data

(62) Division of application No. 12/953,672, filed on Nov. 24, 2010, now abandoned.

(51) Int. Cl.
*G01N 27/407*    (2006.01)

(52) U.S. Cl.
USPC ........... 204/280; 204/424; 204/431; 204/432; 156/277

(58) Field of Classification Search
USPC ........ 204/410, 409, 414, 424, 431, 432, 280; 205/783, 783.5, 784, 784.5, 780.5, 205/781, 787; 73/23.31, 23.32; 156/277
See application file for complete search history.

(56) References Cited

U.S. PATENT DOCUMENTS

| | | | |
|---|---|---|---|
| 6,454,923 B1 * | 9/2002 | Dodgson et al. | 204/415 |
| 7,445,941 B2 * | 11/2008 | Buechler | 436/514 |
| 2002/0166769 A1 * | 11/2002 | Serikov | 204/464 |
| 2007/0154748 A1 * | 7/2007 | Okuyama et al. | 429/17 |
| 2008/0202930 A1 * | 8/2008 | Mett | 204/424 |
| 2009/0162750 A1 * | 6/2009 | Kawakami et al. | 429/218.1 |

FOREIGN PATENT DOCUMENTS

WO    WO 0114864 A2 *    3/2001

* cited by examiner

*Primary Examiner* — Susan D Leong
(74) *Attorney, Agent, or Firm* — Dinsmore & Shohl LLP (57) ABSTRACT

A printed gas sensor is disclosed. The sensor may include a porous substrate, an electrode layer, a liquid or gel electrolyte layer, and an encapsulation layer. The electrode layer comprises two or more electrodes that are formed on one side of the porous substrate. The liquid or gel electrolyte layer is in electrolytic contact with the two or more electrodes. The encapsulation layer encapsulates the electrode layer and electrolyte layer thereby forming an integrated structure with the porous substrate.

11 Claims, 4 Drawing Sheets

PRINTED GAS SENSOR

RELATED APPLICATIONS

This application is a divisional of U.S. patent application Ser. No. 12/953,672 filed Nov. 24, 2010, the entire disclosure of which is hereby incorporated by reference.

TECHNICAL FIELD

The following disclosure relates generally to printed gas sensors, and in particular to a printed gas sensor comprising a liquid, polymer, solid, or gel electrolyte and a method thereof.

BACKGROUND

Electrochemical cells have been used for detection of toxic gases since the 1970s in, for example, fixed location instrumentation for infrastructure (such as buildings and parking garages) and portable safety and inspection equipment used in transportation. For example, see Stetter, J. R., "Instrumentation to Monitor Chemical Exposure in the Synfuel Industry," Annals American Conf. of Governmental and Industrial Hygienists, 11, 225-269, (1984). These sensors may be preferred in ambient monitoring applications because of their accuracy at low detection levels, selectivity, linearity, and power requirements. Industrial-grade electrochemical cells can cost the customer over $25 each and even several hundred dollars without any electronics, even when manufactured in high volumes. This cost can significantly increase the cost of gas monitors and detectors, and can leave manufacturers with few cost-effective options to create ultra-cheap, yet high performance gas detectors. For example, high quality, accurate devices for sensing carbon monoxide and triggering an alarm in the presence of excessive concentrations of carbon monoxide (CO) that may be hazardous to life or health are presently available for many industrial applications, but such devices are still too costly for use in most homes. As a result, less expensive sensors with much lower performance are chosen to meet high volume consumer product cost goals, resulting in lower performance and a sacrifice of needed safety and health protection for the consumer. Additional consumer, medical, and industrial applications will be made available with a significant reduction in the cost and dimensions of electrochemical gas sensors. In some prior art commercial gas sensors, it is necessary to heat the sensing element to elevated temperatures to achieve a fast response time and high sensitivity to objective gases. These sensors are equipped with heaters connected to external power sources, which can use more power than a room temperature gas sensor. Other prior art gas sensors may use a liquid proton conductor where the outside surfaces of the sensing and counter electrodes of the sensor are coated by NAFION™ layers. The lifetime of these sensors can range from about 6-12 months due to rapid drying of the liquid electrolyte. Thus, the sensor requires maintenance due to liquid electrolyte evaporation, leakage, and/or corrosion. In addition, the sensors can have significant manufacturing costs and be relatively large, sometimes with large electrolyte or water reservoirs, so as to not be easily integrated into modern equipment or small personal monitors.

Another prior art gas sensor uses a design incorporating proton conductors, one type of electronically conductive metal catalyst for the sensing electrode, and a different type of electronically conductive metal catalyst for the counter electrode. This allowed the sensing electrode to decompose a gas to produce protons and electrons, while the counter electrode exhibited no activity to decompose the gas. The result is a Nernst potential between the two electrodes, which can be used to detect a target gas. However, some of the issues that could result from such a design include the gas reaction being carried out slowly or interfering reactions can occur on one or the other electrode surface. Additionally, the response signal could be weak. Further, the Nernst potential may not have been or may be difficult to zero in clean air and the calibration is limited to about 59 mV per decade of concentration. Again poor electrolyte or electrode stability over time can degrade performance.

Thus, a competitive electrochemical sensor that can cost less to manufacture in high volume and has high performance and small size, that would create a new opportunity for companies to develop low-cost gas detectors that could be manufactured in high volumes, thus making high accuracy detectors, for example, those that monitor and detect carbon monoxide and protect people and assets, much less expensive. This cost reduction, without loss in performance, could revolutionize and tremendously expand the use of gas detectors in their application, including home carbon monoxide monitors, automobile air quality, and building ventilation and controls. In addition, new applications would become possible, including safety organizations that may desire to inexpensively protect or monitor a large area from toxic gases like carbon monoxide, and universities or scientific/environmental organizations wanting to study toxic gas levels over large areas. In addition, an electrochemical sensor that also can be small can be used in cell-phones to enable worldwide networks of CO and other gas monitors.

While a variety of devices and techniques may exist for detecting gases, it is believed that no one prior to the inventors has made or used the inventive embodiments as described herein.

SUMMARY

In one example, a printed gas sensor is disclosed. The sensor may comprise: a substrate that is at least partially gas porous or gas permeable; an electrode layer, wherein the electrode layer comprises two or more electrodes, with one at least partially porous electrode, that are formed on one side of said porous substrate; a solid, liquid, gel or similarly functional electrolyte layer, wherein the electrolyte layer is in electrolytic contact with the electrode layer, and an encapsulation layer, wherein the encapsulation layer encapsulates the electrode layer and part or all of its substrate and electrolyte layer, thereby forming an integrated structure with the porous substrate.

In another example, a printed gas sensor is disclosed that may comprise: a porous substrate; an electrode layer, wherein the electrode layer comprises two or more porous electrodes that are formed on one side of said porous substrate; a wicking layer formed on the electrode layer; a solid, liquid, or gel electrolyte layer, wherein the electrolyte layer is in electrolytic contact with the two or more electrodes; and an encapsulation layer, wherein the encapsulation layer encapsulates the electrode layer, wicking layer and electrolyte layer thereby forming an integrated structure with the porous substrate.

In still another example, a method for manufacturing a printed gas sensor is disclosed. The method comprises printing two or more electrodes with one at least partially porous electrode onto one side of the at least partially porous substrate using a metal catalyst ink; curing the porous substrate; bonding an optional encapsulation layer having a capillary channel to the porous substrate thereby encapsulating the two or more porous electrodes and forming an electrolyte reservoir; filling the electrolyte reservoir through the capillary channel with a liquid or gel electrolyte; and sealing the capillary channel.

While the specification concludes with claims, which particularly point out and distinctly claim the invention, it is believed the present invention will be better understood from the following description of certain examples taken in conjunction with the accompanying drawings. In the drawings, like numerals represent like elements throughout the several views.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Examples described herein include a printed gas sensor comprising: a porous substrate; an electrode layer, wherein the electrode layer comprises two or more electrodes that are formed on one side of said porous substrate; a liquid or gel electrolyte layer, wherein the electrolyte layer is in electrolytic contact with the two or more electrodes; and an encapsulation layer, wherein the encapsulation layer encapsulates the electrode layer and electrolyte layer thereby forming an integrated structure with the porous substrate. The printed gas sensor may be used to detect and measure a wide range of target gaseous components. By way of example only, it can be used to detect CO, $H_2S$, NO, $NO_2$, $SO_2$ $O_3$, and related compounds that can be either electro-oxidized or electro-reduced compounds. For exemplary electro-oxidized and electro-reduced compounds see: Stetter, J. R. Sang-Do, Han, and G. Korotchenkov, "Review of Electrochemical Hydrogen Sensors," Chemical Reviews 109(3), 2009, pp 1402-1433; Joseph R. Stetter and Jing Li, in Modern Topics in Chemical Sensing: Chapter 4, "Amperometric Gas Sensors—A Review," Chemical Reviews, 108 (2), 2008, pp 352-366; Chang, S. C., Stetter, J. R., Cha, C. S., "Amperometric Gas Sensors", Talanta, 40, No. 4, pp 461-467, (1993).

Figure 4:
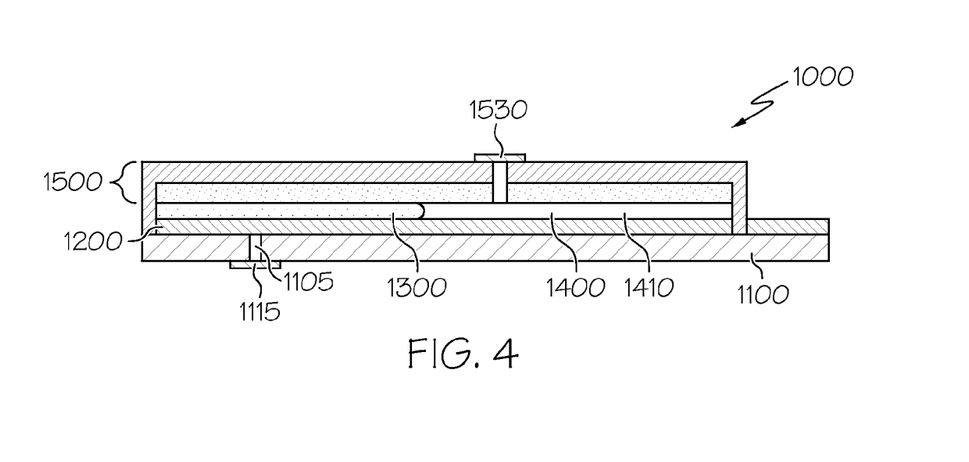
FIG. 4 depicts an exemplary version of a printed sensor in cross section view.
Figure 5:
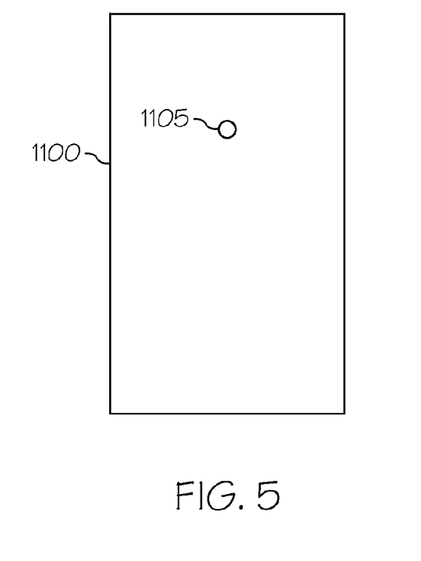
FIG. 5 depicts a substrate layer of the exemplary printed sensor shown in FIG. 4.

The porous substrate is gas permeable at least in part and has porosity sufficient to allow a gas sample to permeate through and react at the working electrode which is also sufficiently porous to allow the sample to diffuse to the metal surface and react. In one exemplary embodiment, the substrate is porous PTFE [trade names like Zitex, Goretex, or MuPor] and the electrode metal material is applied as an ink composite to make a porous gas diffusion electrode. Further, the porous or partially porous substrate may comprise porous polymeric materials, such as porous polytetrafluoroethylene, porous polyethylene, porous polypropylene, porous polyisobutylene, porous polyester, porous polyurethane, porous polyacrylic, porous fluorine polymer, porous cellulosic polymer, porous fiberglass, any other porous non-reactive thermoplastic, or composites or mixtures thereof. The porous substrate thickness can range typically from about 1 to about 10 microns but can be any thickness that allows the appropriate porosity. The porous substrate can be placed on a backplate 220 or support with a controlled-size hole [see FIG. 5] that allows the appropriate gas access into the sensor's working electrode. The thickness of this backplate or support/porous substrate can be 0.002 to 0.005 inches and can comprise PET or Polycarbonate or Polypropylene or other suitable plastic as shown in FIGS. 4 and 5 but any thickness to create the selected or desired gas access is acceptable. The two layers can be laminated, glued or otherwise placed and held adjacent to one another. In another embodiment, the backplate access hole provides the porous entry and obviates the need for a separate and distinct porous or partially porous substrate.

The porous substrate can have an access port for entry of a gas sample to be measured. The access port should be sized to allow a gas sample to enter the sensor, but not too large such that supply of the gas sample is beyond the capacity of the electrodes or the desired range of reactivity. For example, the access port hole may range in size from about 0.003" diameter to about 0.080" in diameter. The larger hole can be desired for lower concentrations e.g. a 1-10 ppm CO sensor while the smaller hole can be chosen for a broader range sensor such as 0-1000 ppm CO sensor. The access port may also be larger or smaller and depend upon the gas to be detected, the range of the sensor desired, and the particular construction and need of the sensing reaction and sensor mechanism of response [e.g., diffusion limited signal, or reaction rate limited signal, or other limitation of the overall electrochemical sensor]. The access port may be formed by, for example, by a stamping process, laser cutting, die cutting, drilling, or other known processes. The access port may be a single hole or a collection of pores or holes or materials that are gas permeable to the analyte. The access port may contain a reactive material to selectively allow the analyte to pass and retain certain unwanted interferences. In operation, a gas sample may enter through the access port and then through the, sometimes optional, porous substrate on the side opposite of the electrode layer in order to reach the working electrode and react. Further, the gas sample may permeate through the access port which can be a straight through hole as shown in the drawings or a tortuous path with or without obstructions or filter materials to allow gas access of the analyte to the working electrode electrolyte interface.

The access port may be covered by a filter, which is adhered to or otherwise held in place next to the substrate. By way of example only, the filter can comprise any material that protects the electrode layer from poisoning or clogging particles or any other unwanted direct exposure to the environment from which the target analyte [that which is to be analyzed] originates. By way of example only, the filter can also comprise any material that can remove the effects of wind and dust, evaporation of the electrolyte from the sensor and reduce effects of pressure fluctuations and air turbulence on the gas sensor. By way of example only, the filter can also comprise any material that may remove interferents, for example, hydrogen sulfide in a CO gas sensor, so that a target gas, CO in this example, may pass through to the electrode layer unimpeded. Examples of a filter can include porous polytetrafluoroethylene (PTFE), impregnated carbon cloth, purafil (purafil is $KMnO_4$ on alumnia) reactive material in the form of powder or gel or composite and a tortuous path. Filters for NO can include triethanolamine on a silica support. As one skilled in the art will appreciate, there are many other chemistries that can be developed for gas sensing.

The electrode layer comprises two or more electrodes that may be designed to provide a high or low surface area to control the electrode-electrolyte interface and maximize the current output of the sensor and minimize the noise in the sensor. The optimum analytical signal for the target analyte will be a combination of considerations of signal and background and noise and interferences. The electrode layer can act as a gas-permeable membrane itself and provide a physical boundary between the electrolyte and the gas. This physical structure of the working electrode is important to control and this control is offered by control of the ink formulation and curing process. The electrode material can also be sputtered or physically or chemically deposited onto or made to lie next to the substrate layer. The electrode layer may be formed on one side of the porous substrate by screen printing or inkjet printing. The thickness of the electrode layer may range from about 100 nanometers to about 125 microns [0.005" or 5 mil] typically but of course can be any thickness that is effective at reacting the analyte. Screen printing typically produces layers that are 0.001-0.005 inches depending on the ink formulation and the screen mesh size used to deposit the composite material. In one exemplary embodiment, screen printing is attractive because it is a fast efficient process and can print multiple electrodes at the same time [i.e. the two or more electrodes needed for sensor operation] and multiple devices on a large substrate area, simultaneously. The materials for the screen printing can be any range of materials needed for the electrode including Pt particles for CO sensors and Au particles for H2S sensors and SWCNT [single walled carbon nanotubes] for Ozone sensors.

The electrode layer only requires two electrodes but more than two are possible. Of the two electrodes, the first electrode may be referred to as the sensing or working electrode and comes into contact with a target gas sample that is to be detected. The second electrode may be known as the counter, auxiliary, counter-reference, or common electrode. When the target gas to be detected comes in contact with the sensing electrode, an oxidation or reduction reaction takes place at the sensing electrode, with a corresponding reduction or oxidation reaction occurring at the counter electrode.

For example, in the case of a carbon monoxide gas sensor, the following oxidation/reduction reaction may occur. Carbon monoxide is oxidized as follows:

$$CO+H_2O \rightarrow CO_2+2H^++2e^- \tag{1}$$

In the corresponding reduction reaction, the protons (hydrogen ions) migrate across a proton conductive electrolyte membrane to a counter electrode where they may react with oxygen as follows:

$$2H^++2e^-+\tfrac{1}{2}O_2 \rightarrow H_2O \tag{2}$$

It may also be important to have an additional or third electrode with a constant or almost constant potential throughout the reaction. Such an electrode may be called the reference electrode and it can play a role in stabilizing the potential of the sensing electrode. Alternatively, the counter electrode may be a non-polarizable counter electrode, which also acts as a reference electrode. The sensor is interfaced to suitable electronic components to read out the current as a measure of the reacting gas concentration. These components can include but are not limited to circuits known as current to voltage convertors, potentiostats, amperostats, and current mirrors, The electrode layer may typically comprise from about 60% to about 90% of a metal catalyst, from about 2% to about 40% of polymer (e.g., micron-sized Teflon particles), in an ink formulation that contains less than about 10% of an optional binder, less than about 10% of an optional surfactant and from about 0% to about 10% of one or more optional modifiers. The metal catalyst may be a powder and, by way of example only, may comprise Pt, Pd, Au, Ag, Ru, Rh, Ir, Co, Fe, Ni, C, or other noble or reactive metals, and alloys or admixtures thereof. The metal catalyst may be a carbon supported catalyst. For example, the carbon support may be nanoparticulate carbon, ball-milled graphitic carbon, single walled carbon nanotubes, Au nanoparticles, or any suitable support. The binder can assist in providing the ink formulation a proper viscosity and vaporization/drying rate for screen printing and/or function to hold the ink to the substrate and merge with the substrate during the curing process to control electrode properties such as hydrophobicity, hydrophilicity or porosity [amount and type]. Suitable binders can be, for example, Nicrobraz-S (available from Wall Colmonoy Corporation located in Madison Heights, Mich.), or solutions of polyvinyl alcohol (PVA) or other polymer or silicate material. The surfactant can act as the solution stabilizer for the ink composite and may comprise solvents, such as water, triton-100, carbopol or other material. The modifiers comprise small amounts of additives, which can be active in controlling the behavior of the inks before, during, and/or after processing and curing. Suitable modifiers may include polyvinyl alcohol, 1-propanol, gum arabic, sodium n-dodecyl sulfate, ethanol, or a composite material. The materials used in the ink composition should generally evaporate or bake out of the composite electrode during a curing process. The materials used in ink composition should generally leave behind an electrode catalyst of the desired porosity, chemistry, density, and hydrophobicity or hydrophilicity for optimum interaction with the electrolyte and analyte gas. Other suitable components for this ink formulation will be apparent to those of ordinary skill in the art in view of the teachings herein on controlling the proper chemical and physical properties of electrodes for gas sensing.

The electrode layer is in electrolytic contact with the electrolyte layer. The electrolyte layer can be any suitable material capable of providing the needed electrolytic system for the sensing and counter reactions and interface to the electrodes. Suitable electrolytes include aqueous systems of acids bases and salts as well as polymer electrolytes like Nafion, or non-aqueous systems like Propylene carbonate Lithium perchlorate or polyethylene oxide Lithium chloride, or ionic liquids. The electrode layer may also be in electrical communication with a measurement device, such as a potentiostat circuit. Electrical communication may comprise the electrode layer having tracks that connect the two or more electrodes to a potentiostat circuit. The electrode layer may be connected to the potentiostat circuit exterior to the gas sensor through the tracks. Electrical communication may also comprise wire connections running from the electrodes through the gas sensor to the potentiostat circuit. An exemplary feature is that the electrode connections run from the active area of sensing at the working electrode inside the sensor to the outside world through a path that is sealed to any material flow [electrolyte, ion, gas, liquid or solid of any kind cannot transport across this seal]. This seal is comprised of a conductor through which electrons can flow but not other material things. It is desired that the senor maintain this property over the lifetime of the sensor which can be months to decades.

The electrolyte layer may be a liquid or gel or solid or composite and is in electrolytic contact with the two or more electrodes of the electrode layer. By way of example only, the electrolyte layer may comprise phosphoric acid, sulfuric acid, aqueous phosphoric acid, aqueous sulfuric acid, methanesulphonic acid, aqueous phosphate salt solution, aqueous sulfate salt solution, potassium hydroxide, aqueous potassium acetate, lithium perchlorate in propylene carbonate, polyvinyl alcohol with sulfuric acid, polyacrylic acid, an ionic gel electrolyte, ionic liquid or any suitable charge carrying entity that will also support the desired electrochemical reactions in the sensors and not create undesired reactions or conditions. Other suitable materials will be apparent to those of ordinary skill in the art in view of the teachings herein.

The electrolyte layer may have a substantially uniform thickness in the printed sensors typically from about 1 mil to about 5 mils [125 microns]. The electrolyte layer may also contain a matrix or gelling agent to prevent dryout or movement during vibration or use or otherwise enhance sensor properties. The electrolyte layer covers at least a part of the sensing electrode area and the counter electrode in the sensor. That is, it is in electrolytic contact with the electrode layer, generally via an electrolyte reservoir formed on at least part of the electrode layer. The electrolyte layer may cover all of the electrode layer or the electrolyte layer may cover part of the electrode layer. The electrode layer may include a chamber adjacent to it to contain additional electrolyte or supporting material to enhance the lifetime or other performance of the electrolyte.

The encapsulation layer encapsulates the electrode and electrolyte layer thereby forming an integrated structure with the porous substrate. The encapsulation layer essentially forms a housing structure with the porous substrate to define an internal region that comprises an electrode and electrolyte layer through which no material may enter or leave [except for the access hole for the analyte which hole is designed to allow analyte access and no material (except gases of course through the gas access port) can leave from the inside of the sensor [i.e., the electrodes or electrolytes]. The encapsulation layer may comprise polyimide, polycarbonate, polyethylene, polypropylene, polyisobutylene, polyester, polyurethane, polyacrylic, fluorine polymer, cellulosic polymer, fiberglass, polytetrafluoroethylene, any other non-reactive thermoplastic, or potting compounds, other materials or mixtures or composites thereof that can be suitably bonded to form the encapsulation. Other suitable materials will be apparent to those of ordinary skill in the art in view of the teachings herein. The encapsulation layer may have a substantially uniform thickness of from about 0.002 to 0.015 inches [2-15 mils] or any size that allows sufficient encapsulation of the sensor. The thickness and nature of the encapsulation and its placement depend upon the size of the sensor, the design and the processes used in the assembly.

The encapsulation layer may further comprise a capillary channel for entry of the electrolyte layer. Such design can expedite electrolyte filling and sensor assembly. The encapsulation layer may further comprise a gas vent hole, which may allow air to exit the electrolyte reservoir as the electrolyte fills it. The gas vent may also serve to allow for venting in applications where there are large pressure fluctuations, for example, gas detection on airplanes or in submarines. By way of example only, the capillary channel and gas vent hole may be formed using plastic film stamping operations, laser cutting or die cutting to create contours and/or holes. The encapsulation should form and not close the gas access design to allow analyte entry as discussed above.

The printed sensor may further comprise a wicking layer that may serve as a separator or absorbent layer between the electrode layer and electrolyte layer, and as a material to wick the electrolyte into the sensor during production and hold the electrolyte against the electrodes. The wicking layer may be screen printed or inkjet printed onto all or a part of the electrode layer. The wicking layer may comprise silicates, silicon carbide, carbon, graphite, fiber glass, polymer, or other inert materials that can form a porous wick. The wicking layer may have a substantially uniform or variable thickness of from about 5 microns to 125 microns in the sensors herein but can be any suitable thickness to allow it to function.

The printed gas sensor may be manufactured by a method comprising: printing two or more porous electrodes onto one side of a porous or partially porous substrate, curing said porous substrate, bonding an encapsulation layer having a capillary channel to said porous substrate thereby encapsulating the two or more electrodes and forming an electrolyte reservoir, filling the electrolyte reservoir with electrolyte through the capillary channel, and sealing the capillary channel. Alternatively, the printed gas sensor may be manufactured by a method comprising: printing two or more porous electrodes onto one side of a porous or partially porous substrate, curing said porous substrate, printing or placing an electrolyte in the electrode area, and then bonding an encapsulation layer to said porous substrate thereby encapsulating the two or more electrodes with electrolyte and thereby forming an electrolyte reservoir [now full], and sealing the entire chamber of electrodes and electrolyte with the gas access being the only route for gas access. Alternatively, the electrolyte reservoir can have a vent formed in it for exceptional pressure change applications. In both cases, the electrolyte and electrode chambers become sealed so that no electrode or electrolyte material can escape the encapsulation except through the access port in the same manner as analyte enters.

The method may further comprise forming a substrate layer from polytetrafluoroethylene, polyethylene, polypropylene, polyisobutylene, polyester, polyurethane, polyacrylic, fluorine polymer, cellulosic polymer, fiberglass, a mixture thereof or any other non-reactive thermoplastic or bondable polymer. The substrate layer may be formed by laser cut, die cut, stamping process, or roll milling or other film forming processing.

The method may further comprise forming an encapsulation layer from polytetrafluoroethylene, polyethylene, polypropylene, polyisobutylene, polyester, polyurethane, polyacrylic, fluorine polymer, cellulosic polymer, fiberglass, a mixture thereof or any other non-reactive thermoplastic polymer or inert single or dual mixture epoxy type encapsulation compounds. The encapsulation layer may be formed by molding, laser cut, die cut, stamping process, or other suitable process.

An ink composition is used to print the two or more electrodes onto one side of a porous substrate. As mentioned above, the ink composition used to print the electrode layer (i.e., two or more porous electrodes) may comprise: from about 60% to about 90% of a metal catalyst, from about 10% to about 50% of a polymer particles (e.g., micron-sized Teflon particles), less than about 10% of a binder, less than about 10% of a surfactant and from about 0% to about 10% of one or more modifiers. The catalyst can comprise noble metals like Pt or Pd or alloys or supported catalysts like Pt on carbon or other supports as such formulations are well known in the art. Printing may be done by screen printing, gravure, or inkjet printing, or other suitable printing technology known in the art that may be used in accordance with the teachings herein. In a screen printing process, the printing screen may comprise stainless steel wire, a plastic mesh, or a platinum mesh across a screen frame. The mesh size may vary depending upon the desired print film thickness, and hence the thickness of the printed two or more electrodes. The area to be screen printed may be patterned on the screen using a desired electrode design template. A squeegee may then be used to spread ink over the screen and the desired pattern is printed on a porous substrate. In an inkjet printing process, it is desired that the formula of the ink be controlled so that the ink remains printable for some time on the screen and does not dry too fast. The added retardant should control this process and one exemplary embodiment herein uses a PVA/water solution as the retardant or modifier additive to the metal-plastic ink composite formula.

The method may further comprise a curing step where the sensor ink and porous substrate may be cured by heating or drying, for example, at about 150° C. for about 10 minutes in an oven. Further curing when using PTFE may require additional heating to about 280-300 C for one hour to form a suitable cured and porous diffusion electrode for gaseous reactions. The curing step may be used to remove any solvent present. Remaining solvent not removed during this step may cause problems by polluting the atmosphere surrounding the sensor element. Curing may be performed by, for example, forced air drying (e.g., at elevated temperatures), infrared irradiation, ultraviolet irradiation, ion-beam irradiation, gamma irradiation, and combinations thereof. The curing step is chosen to fix the electrode structure in whatever remaining composite porous or partially porous electrode exists. In one exemplary embodiment for CO, for example, the mixture of PTFE particles [30%] and Pt particles [60%] and Nicobraz binder [10%] is cured at 300° C. for one hour to create a CO electrode with a very useable porosity and hydrophilicity/hydrophobicity for measurement of CO in air at 1-1000 ppm.

The method may further comprise printing a wicking layer onto the two or more electrodes and/or porous substrate. Printing of the wicking layer may be accomplished by screen printing or inkjet printing using a slurry of ink comprising nanoparticulate wick material. As mentioned above, the nanoparticulate wick material may comprise silicates, silicon carbide, carbon, graphite, fiber glass, or other porous materials of fibrous materials that when matted together form pores or wickable substrates. The wicking ink may also comprise silica-based filter paper that is ground or mashed into small particles and mixed with water or water with an added salt, acid or base. The composition has sufficient water and vehicle [e.g. PVA, Nicobraz or other retardant] to make an ink suitable for printing.

The bonding of an encapsulation layer or substrate layer may comprise thermal bonding, chemical bonding, adhesive bonding, ultrasonic bonding, lamination, pressure bonding, o-ring bonding or welding. Once the encapsulation layer is bonded to the porous substrate thereby forming an electrolyte reservoir, the electrolyte reservoir is filled. Filling may be done by submerging the capillary channel or the entire printed sensor in electrolytic solution. As the capillary channel or printed sensor is submerged, electrolytic solution rises through the capillary channel and into the electrolytic reservoir. Once inside the reservoir, the wicking layer, if present, may capture some of the electrolyte thereby holding it against the electrode. After the reservoir is filled, the capillary channel and any vent holes may be sealed by, for example, thermal sealing, chemical sealing, adhesive sealing (e.g., epoxy). When wicking is used, a vent is desired for the air to flow out and this should also be sealed at the end. This seal can be potting materials or a gas porous vent to be used for equalization of pressure when the sensor is used for pressure change applications.

The resulting printed gas sensor may be of various sizes and dimensions. For example, the thickness of the printed gas sensor may be less than about 1000 micron [about 1 mm] or less thick. We have constructed the prototype sensors where the total thickness of all layers is about 500 microns thick. For convenient testing, the initial prototypes are about ¼ to ½ inch square and ½ mm thick. But since the resolution today for silk screening is about 1-10 microns and getting better all the time, we envision that ⅛, or even 1/16 inch square sensors may be possible with the approach described herein.

The gas sensor performance of the exemplary CO electrodes demonstrated herein may have a measurement range of from about 0 ppm to about 1000 ppm CO. In another example, the gas sensor performance for CO may have a measurement range of from about 0 ppm to about 500 ppm. The measurement output signal from the screen-printed CO electrode in the gas sensor may range from about 5 nanoamps/ppm to about 25 nanoamps/ppm. The measurement output signal from the gas sensor may also range from about 10 nanoamps/ppm to about 25 nanoamps/ppm. These signals are altered by choosing the size of the gas access port size and can be made much smaller with smaller holes for gas access. The gas sensor may produce a measurement response time of less than about 30 seconds at 20° C. The gas sensor may also produce a measurement response time of less than about 20 seconds at 20° C. Thinner sensors could have even faster response times becuase diffusion times are faster because diffusion distances are shorter. For example, electrolyte volumes herein still produce a very stable sensor even under condition of near 0% RH for a long time giving this printed sensor a long lifetime in field use for CO monitoring.

In one exemplary embodiment for CO monitoring, the printed gas sensor electrochemically senses gases using an electronic circuit called a potentiostat. In the potentiostatic method or mode, the gas to be quantitatively sensed or detected may contact the sensing or working electrode in the presence of an electrolyte, and generate a current that is proportional to the amount of target gas entering the cell. The common or counter electrode can run the complementary half-cell reaction. The reference electrode operating in a potentiostatic circuit can maintain the thermodynamic potential of the working electrode during sensing. Simple electronics may be interfaced to the sensor to convert the current to a voltage for meter or recorder readout.

Figure 1:
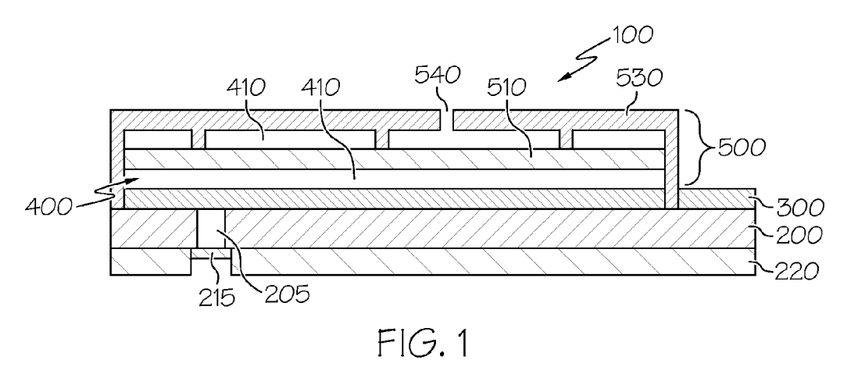
FIG. 1 depicts an exemplary version of a printed sensor in cross section view.
Figure 2A:
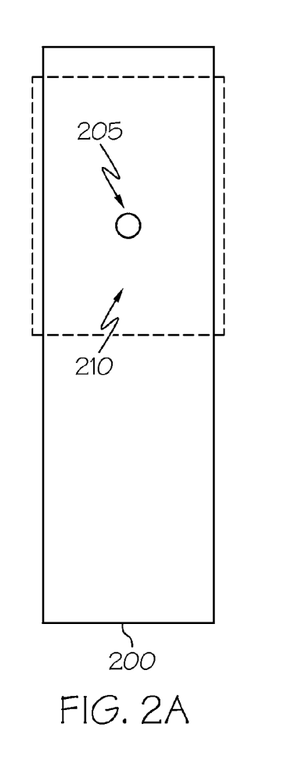
FIGS. 2A & 2B depict a substrate layer of the exemplary printed sensor shown in FIG. 1.
Figure 2B:
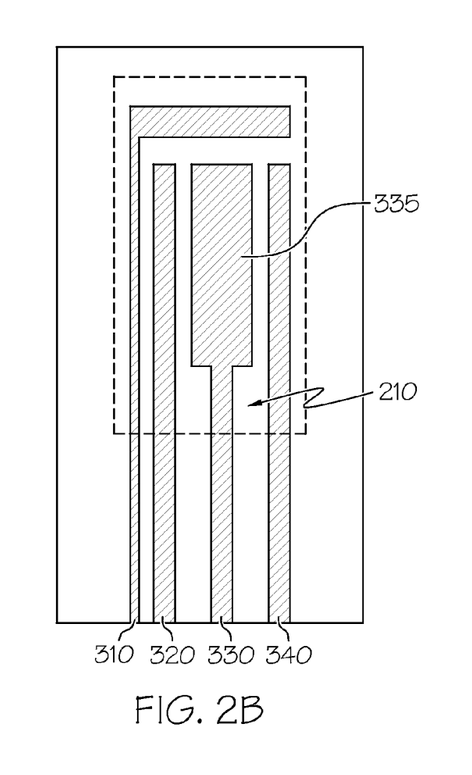
Figure 3A:
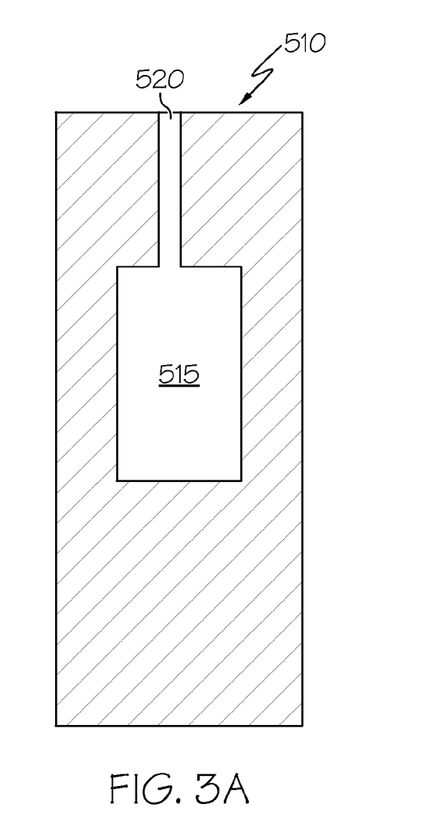
FIGS. 3A & 3B depict an encapsulation layer of the exemplary printed sensor shown in FIG. 1.
Figure 3B:
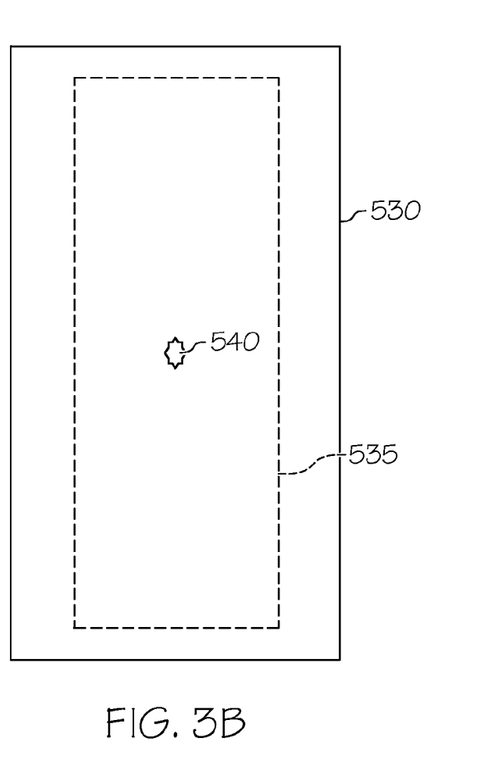

Turning to the figures, FIGS. 1-3 depict an example of a printed gas sensor operable to detect and measure carbon monoxide levels. Of course, other target gases that may be detected and/or measured using the printed gas sensor will be apparent to those of ordinary skill in the art in view of the teachings herein. Further, while exemplary geometries have been disclosed, other geometries will be possible to those of ordinary skill in the art. In addition, while exemplary combinations of ink properties [viscosity, composition, drying rate, etc.] and ink structure [thickness, porosity, etc.] have been disclosed for the exemplary sensors, one of ordinary skill in the art can envision other inks and compositions and properties and structures. While exemplary combination of these specially designed parts with the printing processes and assembly processes have been disclosed, alternatives will become obvious to those skilled in the art for the design and assembly of a family of related electrochemical gas sensors by this new approach that combines the many special features of materials and processes described herein. Referring to FIG. 1, an exemplary version of printed gas sensor 100 is shown. The printed gas sensor 100 shown comprises: a porous substrate 200; an electrode layer 300; a liquid or gel electrolyte layer 400 in electrolytic contact with the electrode layer 300; and an encapsulation layer 500 that encapsulates the electrode layer 300 and electrolyte layer 400 thereby forming an integrated structure 100 with the porous substrate 200. In this example, the substrate layer 200 comprises porous polytetrafluoroethylene, though other porous materials may be used with porosity desirably in the region 205 for gas access, and has four electrodes shown printed onto one side of the porous polytetrafluoroethylene substrate 200. If porous PTFE is used, the porosity can be filled with adhesive or a back-plate or similar approach as long as porosity remains in the desired gas access area, 205. The porous PTFE is a convenient substrate for the gas sensor electrode but can be difficult for printing [a special method/ink may be needed as disclosed herein]. The substrate layer 200 has an access port 205 for entry of a gas sample to be measured, and an optional filter 215 covering the access port 205 can be made of virtually any shape and size to enhance sensor operation in applications. Also illustrated in FIG. 1, is an optional backplate 220. The backplate can be utilized to block gas access to the entire substrate 200 except for an opening corresponding to the access port 205. This layer 220 is illustrated not to scale and can be very thin in nature or just fill the pores totally or partially in layer 200.

As further depicted in FIGS. 2A & 2B, the electrode layer 300 is shown having a test electrode 310, reference electrode 320, working (or sensing) electrode 330 and counter electrode 340 formed on one side of said porous substrate 200, the side opposite to the gas access and optional filter. It should be understood that, like other components and features described herein, test electrode 310 and reference electrode 320 may be omitted entirely if desired or not needed by the sensing system. The substrate layer 200 also depicts the area 210 to be encapsulated by the encapsulation layer 500. The electrolyte layer 400 is within the encapsulation layer.

The test electrode 310 may allow the printed gas sensor to self-test for degradation or failure of the working electrode 330 (and therefore, the ability of the printed gas sensor 100 to accurately sense and measure a target gas concentration) and be aware of sensor condition. The test electrode 310 may be arranged to sense a gas normally present in the atmosphere, e.g., oxygen, to detect the decomposition of the electrodes or electrolyte or provide added temperature compensation capability or similar performance enhancements over time. The test electrode 310 may also be arranged to generate a test gas within the sensor and in a controlled amount to effect a test of the operation of the sensor (i.e., working electrode 330). The test electrode 310 may comprise a catalyst comprising Pt, Pd, Au, Ag, Ru, ruthenium dioxide, Cr, Mn, Fe, Co, Carbon, or combinations or alloys or composited suitable to the need and function in the sensor.

In this example, the working electrode 330 has a sensing area 335 and is comprised of a platinum metal catalyst composite for CO sensing, though other metal catalysts may be used as disclosed above for CO or for other gas sensors. The reference electrode 320 may be comprised of Pt composite or Ag/AgCl, or Pb/PbO2 or other material suitable to the sensor design. In this particular example for a CO sensor, Pt-black composite is used. The counter electrode 340 may be comprised of Pt, or Au, or Pb/PbO2 or any suitable material for the particular sensor. In this particular example, a CO sensor with Pt-Black and Teflon particle composite is used.

The electrolyte layer 400 is in electrolytic contact with the electrode layer 300 and comprises lithium perchlorate in propylene carbonate or alternatively polyvinyl alcohol with sulfuric acid or sulfuric acid in a porous glass or porous plastic matrix. The electrolyte layer 400 covers the sensing area 335 of the working electrode 330 and extends to the other sensor electrodes such that all electrode in the sensor are in electrolytic contact (i.e. in contact through the electrolyte). In some cases, it may also be desirable for the thin film electrolyte to be in contact with an electrolyte reservoir 410 formed on or over the electrode layer 300 and it may be formed in a section of the encapsulation layer.

The encapsulation layer 500, as shown in FIG. 1, encapsulates the electrode 300 and electrolyte layer 400 thereby forming an integrated structure with the porous substrate 200. As further depicted in FIG. 3A, encapsulation layer 500 comprises a capillary channel layer 510 having a capillary channel 520 for entry of the electrolyte layer. Capillary channel layer 510 also defines a bucket volume 515 where electrolyte can reside during expansion from accumulated moisture from the air. The capillary channel layer is an optional component to the operation of the sensor The encapsulation layer 500 may further comprise a cap layer 530 having a gas vent hole 540, as depicted in FIG. 3B. The gas vent is useful for filling the electrolyte in one exemplary embodiment and for applications wherein the sensor is used and the pressure is changed of the sensed ambient at a certain rate. The capillary channel layer 510 and cap layer 530 shown were laser cut from polypropylene be formed using plastic film stamping operations in this example, laser cutting or die cutting to create contours and/or holes. The two layers are packaged together by heat sealing them together or alternatively by adhesive bonding, and then the two layer package is heat sealed or otherwise bonded to the porous substrate layer 200. It is desired that the electrode or a conductor emerge through the encapsulation so that external contact to the electrodes encapsulated within is made. The connection means can be by conductor wire or conductive plastic or any material that is a conductor and can be sealed such that the electrode and electrolyte materials cannot escape from the senor over many years time. The cap layer 530 also depicts the area 535 to be encapsulated and the area where the heat sealing will take place. While the encapsulation layer is shown having two sub-layers, it should be understood that the encapsulation layer may comprise one layer having a capillary channel, bucket volume, and gas vent or any other optional feature formed therein. Pre-forming these features should save assembly time and cost in manufacture.

FIGS. 4-7 depict another example of a printed gas sensor operable to detect and measure carbon monoxide levels. Referring to FIG. 4, an exemplary version of a printed gas sensor 1000 is depicted. The printed gas sensor 1000 shown may measure carbon monoxide levels, however, other target gases may be used. Sensor 1000 comprises: a porous substrate 1100; an electrode layer 1200; a wicking layer 1300, a liquid or gel electrolyte layer 1400 in contact and permeating the wick 1300 and in electrolytic contact with the electrode layer 1200; and an encapsulation layer 1500 that encapsulates the electrode layer 1200, wicking layer 1300 and electrolyte layer 1400 thereby forming an integrated structure with the porous substrate 1100.

As further depicted in FIG. 5, the substrate layer 1100 comprises porous polytetrafluoroethylene, though other porous materials may be used, and has a gas access hole 1105 where the porosity of the PTFE is maintained and everywhere else can be closed off either by a substrate plastic bonded to it or by additives painted on it, and a filter 1115, seen in FIG. 4, covering the gas access hole which can be a plastic part used to close off the porous PTFE from the ambient everywhere except the gas access part. Note that the gas access part is preferred to align with the working electrode printed on the opposite side of the porous PTFE. The substrate 1100 is further shown in FIG. 6 having four electrodes printed onto it. The electrode layer 1200 is shown having a test electrode 1210, reference electrode 1220, working (or sensing) electrode 1230 and counter electrode 1240 formed on one side of said porous substrate 1100. As mentioned above, test electrode 1210 and reference electrode 1220 may be omitted entirely if desired. The substrate layer 1100 also depicts the area 1110 to be encapsulated by the encapsulation layer 1500.

Figure 6:
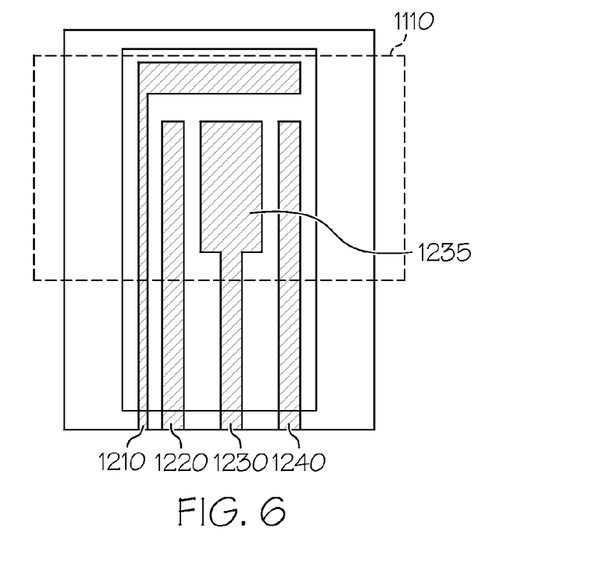
FIG. 6 depicts a substrate and electrode layer of the exemplary printed sensor shown in FIG. 4.
Figure 7:
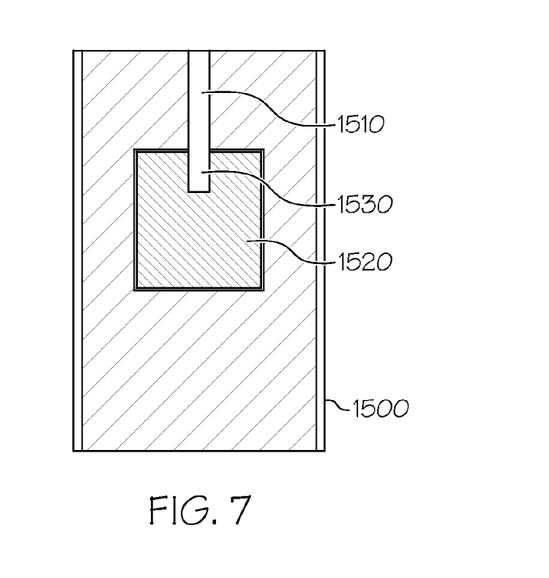
FIG. 7 depicts an encapsulation layer of the exemplary printed sensor shown in FIG. 4.

In this example, the working electrode 1230 has a sensing area 1235, and is comprised of a platinum metal catalyst, though other metal catalysts may be used as disclosed above. The counter electrode 1240 may be comprised of Pt-black-PTFE porous electrode composite in this particular example also for a CO sensor to result.

The wicking layer 1300 of exemplary printed sensor 1000 is shown in FIG. 4. The wicking layer 1300 may be screen printed or inkjet printed onto the electrode layer 1200. The wicking layer 1300 may comprise silicates, Nafion, silicon carbide, carbon, graphite, glass fiber filter paper, porous polypropylene, or even Teflon or other battery separator type materials that will wick and hold electrolyte against the electrodes in the sensor; such materials are typically chosen to be compatible with the electrolyte.

As depicted in FIG. 4, the electrolyte layer 1400 is in electrolytic contact with the electrode layer 1200 and comprises lithium perchlorate in propylene carbonate or alternatively polyvinyl alcohol with sulfuric acid, polyethylene oxide and lithium chloride, ionic liquids, acetic acid with certain salts or KCl or sodium, potassium or cesium hydroxide solutions. The electrolyte layer 1400 covers the sensing area 1235 of the working electrode 1230. That is, it provides electrolytic contact with the electrodes in the electrode layer 1200, and generally via an electrolyte reservoir 1410 which is an empty, unfilled portion of the electrolyte layer formed within the encapsulation area 1500. In one further embodiment, an electrode contact area 1250 is outside the encapsulation area 1500 wherein the electronic contact us made to the electrodes.

The encapsulation layer 1500, as shown in FIG. 4, encapsulates the electrode layer 1200, wicking layer 1300, and electrolyte layer 1400 thereby forming an integrated structure with the porous substrate 1100 through which no materials can pass over long times. The encapsulation layer 1500, as further depicted in FIG. 7, comprises a capillary channel 1510, a bucket volume 1520 and a gas vent hole 1530. The capillary channel layer 1510 and bucket volume 1520 shown were formed from polypropylene using a plastic film stamping operation to create the contours. The gas vent hole was laser cut. The encapsulation layer 1500 was heat sealed to the porous substrate layer 1100. These features allow for convenient filling with electrolyte solution but are not required if the wicking layer already contains the electrolyte or the electrolyte is placed over the electrodes before encapsulation steps are taken.

Figure 8:
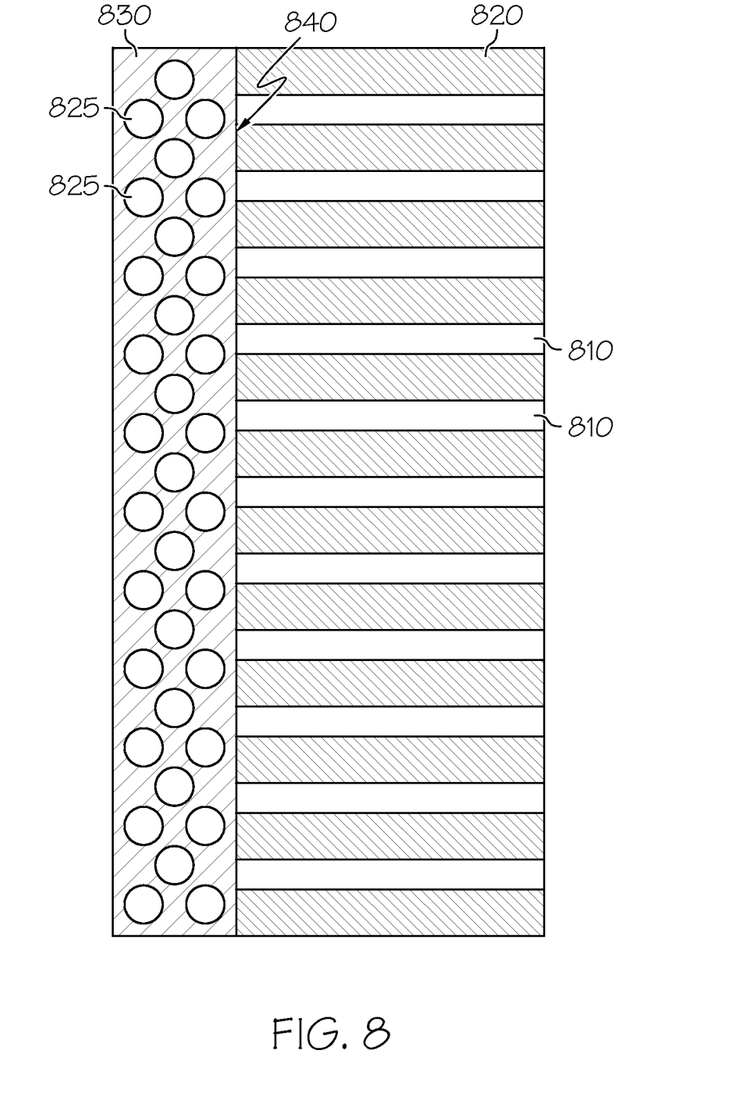
FIG. 8 depicts an exemplary electrochemical reaction in the porous gas electrode.

Referring to FIG. 8, the electrochemical reaction zone for a gaseous analyte that has been created in the exemplary sensors of FIGS. 1-3 & 4-7 is depicted. The carbon monoxide electrochemical reaction takes place in the working electrode at the triple phase boundary 840 of the metal catalyst (surface of the working electrode), the electrolyte [touching the surface of the working electrode], and the gas also arriving at and touching the surface of the electrode and electrolyte and perhaps being considered dissolved in the electrolyte in the triple phase boundary region. As shown in FIG. 8, the carbon monoxide gas 810 entering through the gas access hole and through the pores of a porous PTFE substrate 820 and contacting the catalyst particles 825 that are at least partially wetted with electrolyte 830.

While several devices and components thereof have been discussed in detail above, it should be understood that the components, features, configurations, and methods of integrating and using the devices discussed are not limited to the unique contexts provided above. In particular, components, features, configurations, and methods of use described in the context of one of the devices may be incorporated into or out of any of the other devices. Furthermore, not limited to the further description provided below, additional and alternative suitable components, features, configurations, and methods fabricating and of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. A method of manufacturing a printed gas sensor, the method comprising:
   printing two or more porous electrodes onto one side of a partially porous substrate using a metal catalyst ink;
   curing the partially porous substrate and printed electrodes;
   bonding an encapsulation layer to the partially porous substrate thereby encapsulating at least a portion of the two or more porous electrodes and forming an electrolyte reservoir;
   filling the electrolyte reservoir with a liquid or gel electrolyte,
   wherein the metal catalyst ink comprises 30% PTFE particles, 60% Pt particles and 10% binder.

2. The method of claim 1, wherein the encapsulation layer comprises a capillary channel, and wherein the filling the electrolyte reservoir utilizes the capillary channel; and wherein the method further comprises:
   sealing the capillary channel.

3. The method of claim 1, wherein the method further comprises printing a wicking layer onto a portion of the two or more electrodes.

4. The method of claim 1, wherein printing two or more porous electrodes comprises screen printing, gravure, or inkjet printing.

5. The method of claim 3, wherein printing the wicking layer comprises screen printing or inkjet printing.

6. The method of claim 1, wherein bonding the encapsulation layer comprises thermal bonding, chemical bonding, adhesive bonding, ultrasonic bonding, lamination, pressure bonding, o-ring bonding or welding.

7. The method of claim 1, wherein filling the electrolyte reservoir comprises submerging the electrolyte reservoir in an electrolytic solution.

8. The method of claim 2, wherein sealing comprises thermal sealing, chemical sealing, adhesive sealing or welding.

9. The method of claim 1, wherein curing comprises heating, heating in a controlled atmosphere, forced air drying, infrared irradiation, ultraviolet irradiation, vacuum drying-ion-beam irradiation, gamma irradiation, and combinations thereof.

10. The method of claim 1, wherein the method further comprises forming a substrate layer from porous polytetrafluoroethylene, porous polyethylene, porous polypropylene, porous polyisobutylene, porous polyester, porous polyurethane, porous polyacrylic, porous fluorine polymer, porous cellulosic polymer, porous fiberglass, or a mixture thereof.

11. The method of claim 1, wherein the method further comprises forming an encapsulation layer comprises polytetrafluoroethylene, polyethylene, polypropylene, polyisobutylene, polyester, polyurethane, polyacrylic, fluorine polymer, cellulosic polymer, fiberglass, or a mixture thereof.

* * * * *